United States Patent [19]
Lang

[11] Patent Number: 5,609,572
[45] Date of Patent: Mar. 11, 1997

[54] CASSETTE INFUSION SYSTEM

[76] Inventor: Volker Lang, Zugspitzstrasse 52, 82131 Gauting, Germany

[21] Appl. No.: 256,326

[22] PCT Filed: Nov. 23, 1993

[86] PCT No.: PCT/EP93/03286

§ 371 Date: Jul. 8, 1994

§ 102(e) Date: Jul. 8, 1994

[87] PCT Pub. No.: WO94/12225

PCT Pub. Date: Jun. 9, 1994

[30] Foreign Application Priority Data

| Nov. 23, 1992 | [DE] | Germany | 42 39 285.3 |
| Mar. 26, 1993 | [DE] | Germany | 43 09 972.6 |
| May 26, 1993 | [DE] | Germany | 43 17 430.2 |
| Sep. 7, 1993 | [DE] | Germany | 43 30 203.3 |
| Oct. 25, 1993 | [DE] | Germany | 43 36 336.9 |

[51] Int. Cl.$^6$ ................................................ A61M 1/00
[52] U.S. Cl. ........................................................ 604/22
[58] Field of Search ................................ 604/65–67, 153, 604/246, 30–34, 49, 50, 51–53, 118, 247–249

[56] References Cited

U.S. PATENT DOCUMENTS

| 4,142,524 | 3/1979 | Jassanolla et al. | 604/153 |
| 4,152,098 | 5/1979 | Moody et al. | 604/153 |
| 4,456,009 | 6/1984 | Vcelka et al. | 604/152 |
| 4,474,309 | 10/1984 | Solomon | 604/152 |
| 4,519,792 | 5/1985 | Dawe | 604/152 |
| 4,842,584 | 6/1989 | Pastrone | 604/153 |
| 4,846,636 | 7/1989 | Danby et al. | 128/DIG. 13 |
| 5,098,262 | 3/1992 | Weeker et al. | 604/153 |
| 5,108,367 | 4/1992 | Epstein et al. | 604/67 |

Primary Examiner—Manuel Mendez
Attorney, Agent, or Firm—Morgan & Finnegan, L.L.P.

[57] ABSTRACT

A modular cassette infusion system for multiple infusions and the automatic administration of medicament. Sterile disposable cassettes are employed, which possess integral connections for the infusion lines, inlet valves, liquid distribution ducts, pump chambers, outlet valves, venting filters and chambers for the measurement of the infusion pressure. The system renders possible the infusion of 3, 6 or more different infusion solutions and medicaments held in disposable syringes via one or more small-volume pump chambers with outlet valve separately via a plurality thereof in parallel via only one vascular access point to the patient with the correct volume in a pulsating manner or in very small individual quantities substantially continuously in a quick succession one after the other without incompatible medicaments being mixed. After insertion in an universal, electromechanical and pneumatic or only electromechanical or furthermore electrohydraulic valve pump syringe actuating device the cassettes are operated with the aid of pressure surges. Since for control an electronic microprocessor control device is utilized, which can furthermore produce a printed record of an infusion and since a compatibility with other infusion equipment, as for example injection pumps is provided for, fixed programs and manual programming steps may solve the most types of infusion problem and provide for a substantial reduction in the work to be performed by nursing staff with an accompanying substantial reduction in costs. Additionally substantially enhanced improved patient safety is ensured.

34 Claims, 9 Drawing Sheets

CASSETTE INFUSION SYSTEM

FIELD OF THE INVENTION

The invention relates to a cassette infusion system based on the basis of the modular design principle for multiple infusions and the automatic administration of medicaments with a special suitability for intensive care.

BACKGROUND OF THE INVENTION

In the case of current modern intensive medical care using intravascular infusion therapy, such thereby usually takes place through an infusion catheter which requires 3, 6 or more infusion devices and solutions in order to ensure the necessary supply of different nutrients such as amino acids, carbohydrates, fats as well as vitamins, minerals and various different medicaments. For this purpose, at the present time, there is an increasing use of expensive infusion pumps, either alone or frequently for reasons of price, in combination with gravity infusion systems. The production of such infusion systems however necessitates a multiplicity of sterile disposable articles such as for example special hose systems with wide lumen infusion syringes, drip chambers, regulators, connecting hose with check valves, hose unions and manifolds, 3 way cocks etc. which involve complex manual operations. The result is however a highly unsystematic, expensive overall hose arrangement involving generally known risks such as confusion of infusion lines and infusion solutions, wrong operation of the 3 way cocks with retrograde infusion hoses and infusion containers, bacterial contamination in the course of manual assembly, errors in the times and volumes of application of the desired infusion solutions, incompatibility problems between medicaments and excessively voluminous hoses and other difficulties.

European patent publication 288 716 B1 has already disclosed a cassette infusion system, whose cassette housing contains a flow through passage, several selectively operated valve devices, a pump chamber and corresponding liquid inlets along the longitudinal direction of the through passage for connection with infusion devices. This cassette system does, however, suffer from the disadvantage that it is an integrated system and not capable of adaptation.

One object of the invention is to create a cassette infusion system, which is adaptable in use and can be employed for the administration of medicaments.

SUMMARY OF THE INVENTION

In accordance with the invention this object is to be attained by employing the features recited in claim 1. Accordingly the cassette infusion system in accordance with the invention and based on the modular design principle for multiple infusion possesses a particular suitability for intensive medical care. The individual modules thereof comprise at least the following ones:

a) an infusion pump cassette with at least one pump chamber and at least one outlet valve and b) an infusion distributor cassette, which has two or more connections for infusion lines with associated inlet valves and following liquid distribution ducts, which open into one or more outlet connections.

The infusion pump cassette may additionally comprise a pressure measuring chamber and at one least venting filter.

As an additional module, a medicament application cassette, may be present which comprises a plurality of medicament containers. When it includes such a medicament administration cassette, the system may also be integrally designed as a system comprising at least one pump, liquid distribution ducts and the associated lines and valves.

Further modules can include a valve, pump and syringe actuating device, which by means of electromechanically and/or pneumatically or, respectively, electropneumatically and/or hydraulically or, respectively, electrohydraulically actuated plungers controls the valves arranged in the cassettes and the pump chambers and via metering plungers determines the infusion pressure and also a microprocessor control device.

Further preferred designs according to the invention will be comprehended from the claims dependent on claim 1.

The cassette infusion system more particularly renders possible a flexible adaptation to the respective requirements of the patient.

In this respect, it is, for example, possible to supply the patient with two or more incompatible infusion solutions using merely one vascular access point. Using a preselectable program, it is possible to swill out the cassette, the duct and the hose system with an indifferent flushing solution, such as for instance physiological saline solution, prior to switching over to the next, incompatible solution. The vascular access points may be better kept open by programmed "intermittent flushing" in the course of the infusion. In this case, a preselected program enables the user to quickly evacuate the pump chamber in one, two or three steps as preselected in intervals which may be programmed in time in the case of continuous infusion.

Using a suitable programming control it is possible for the vascular access points also to be maintained open by pulsating infusion. In this respect the respective individual quantities may be programmed in accordance with the volume thereof and the frequency per unit time. Because of the sterile disposable cassettes and a valve pump and syringe actuating device, which is easily kept clean, hygiene can be improved.

Operation may be simplified by a universal actuating device, which according to respective requirements renders possible the use of different infusion distribution cassettes, pump cassettes with one or more multiple pump chambers with or without a combined medicament administration cassette.

The above described system is for example basically furthermore suitable for peritoneal dialysis. In the case of such application the pump chamber will have a volume adapted for this purpose.

Further details of the invention will be understood from the working examples with reference to the drawings.

DETAILED DESCRIPTION OF THE INVENTION

Figure 9:
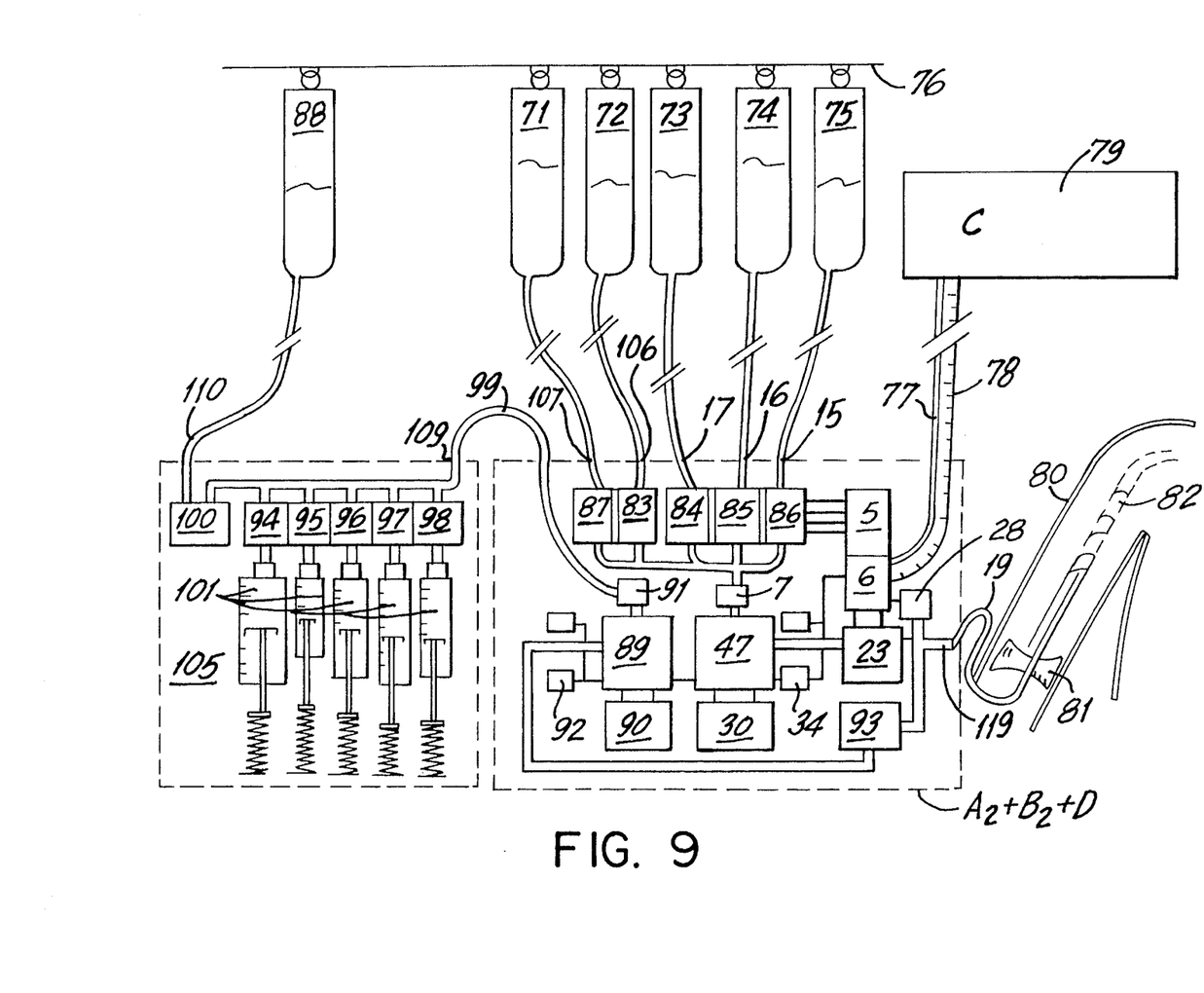
FIG. 9 shows a diagram of the function of the individual modules of one embodiment of the cassette infusion system of the invention.

The cassette infusion system described herein with reference to a working embodiment comprises five modules, that is to say the parts A, B, C, D and E as depicted in FIG. 9.

Figure 1:
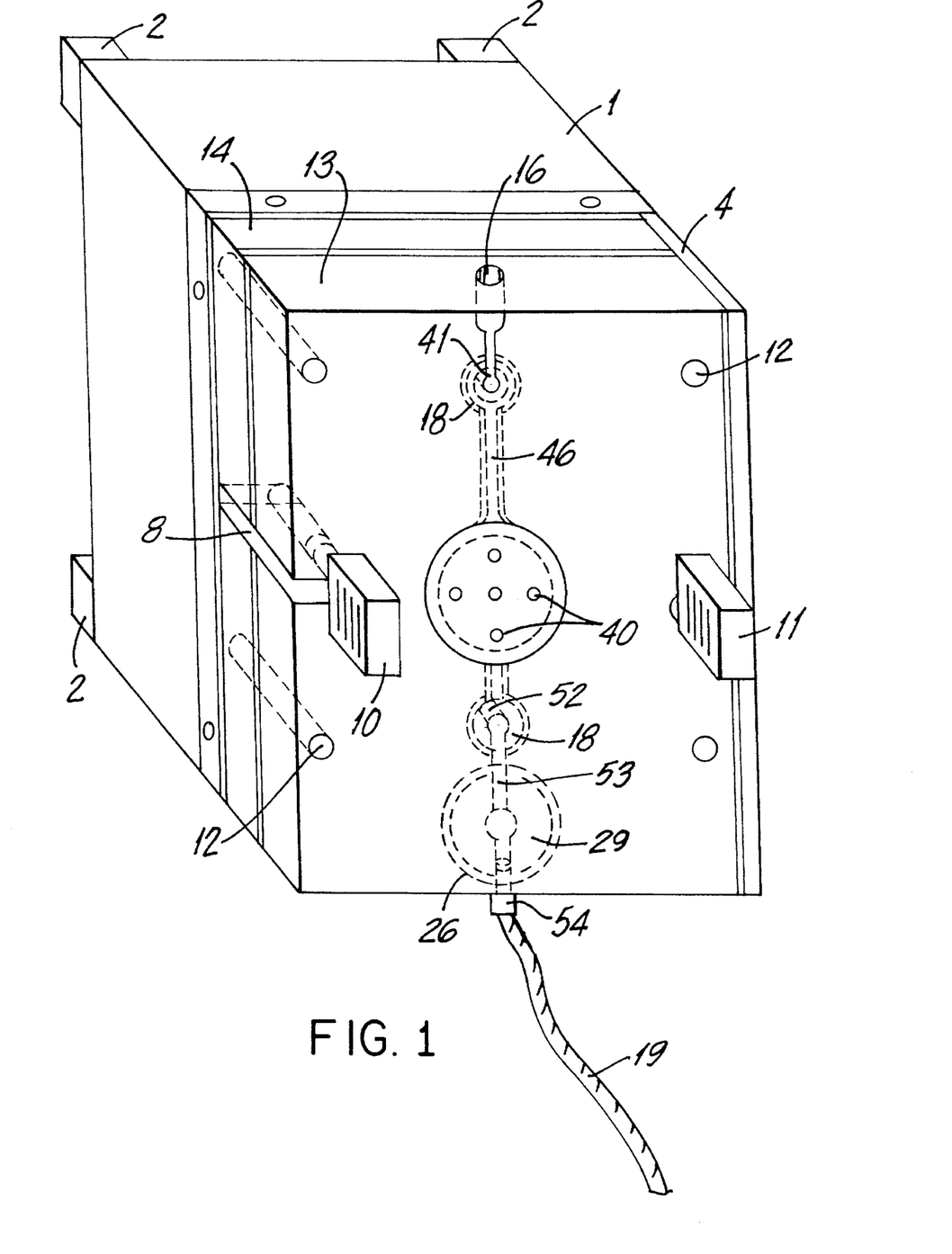
FIG. 1 shows a pump actuating device of the cassette infusion system with a infusion pump mounted thereon.

FIG. 1 shows an electropneumatically operating valve and pump actuating device B1 for an infusion pump cassette A1. The form illustrated is the simplest design of a pump actuating device, which is merely designed for a pump with a pump chamber and accessories, the infusion pump cassette being in the mounted condition.

A cover hood 1 of a lower part of the pump actuating device with support feet 2 is permanently connected with a part 4 serving as an abutment and a mounting plate 24. In the holder section produced as a result, the infusion pump cassette is inserted. It is additionally thrust, by the clips 10 and 11, which have tension springs and snap into the slots 8, firmly against the underlying part, i.e. the mounting plate 24 of the pump housing, as depicted in FIG. 2.

A base plate 14 and a cover plate 13 of the infusion pump cassette are fitted together by means of welded-on bolts 12 and sealing strips 20 (see FIG. 5), elastic valve plates 18 and a pressure measuring diaphragm, which are arranged between them, being thrust together. On the transparent cassette cover plate 13, it is possible to see on the top the conical connection opening 16 for the Luer connection cone of a commercially available, standard infusion set of fittings.

The same is continued in a duct in the respective valve seat 41 shown in broken lines, which in FIG. 1 is illustrated from the rear side. From this point there extends a duct 46 to the pump chamber 47, not illustrated in FIG. 1, which is arranged underneath the venting openings 40, illustrated in FIG. 1, of a venting filter. FIG. 1 furthermore shows a valve seat 52 of a discharge valve and a following connecting duct 53 leading to a pressure measuring chamber 26 and to the connection opening 54 for the Luer connection cone of an infusion hose 19 leading to the patient.

Figure 2:
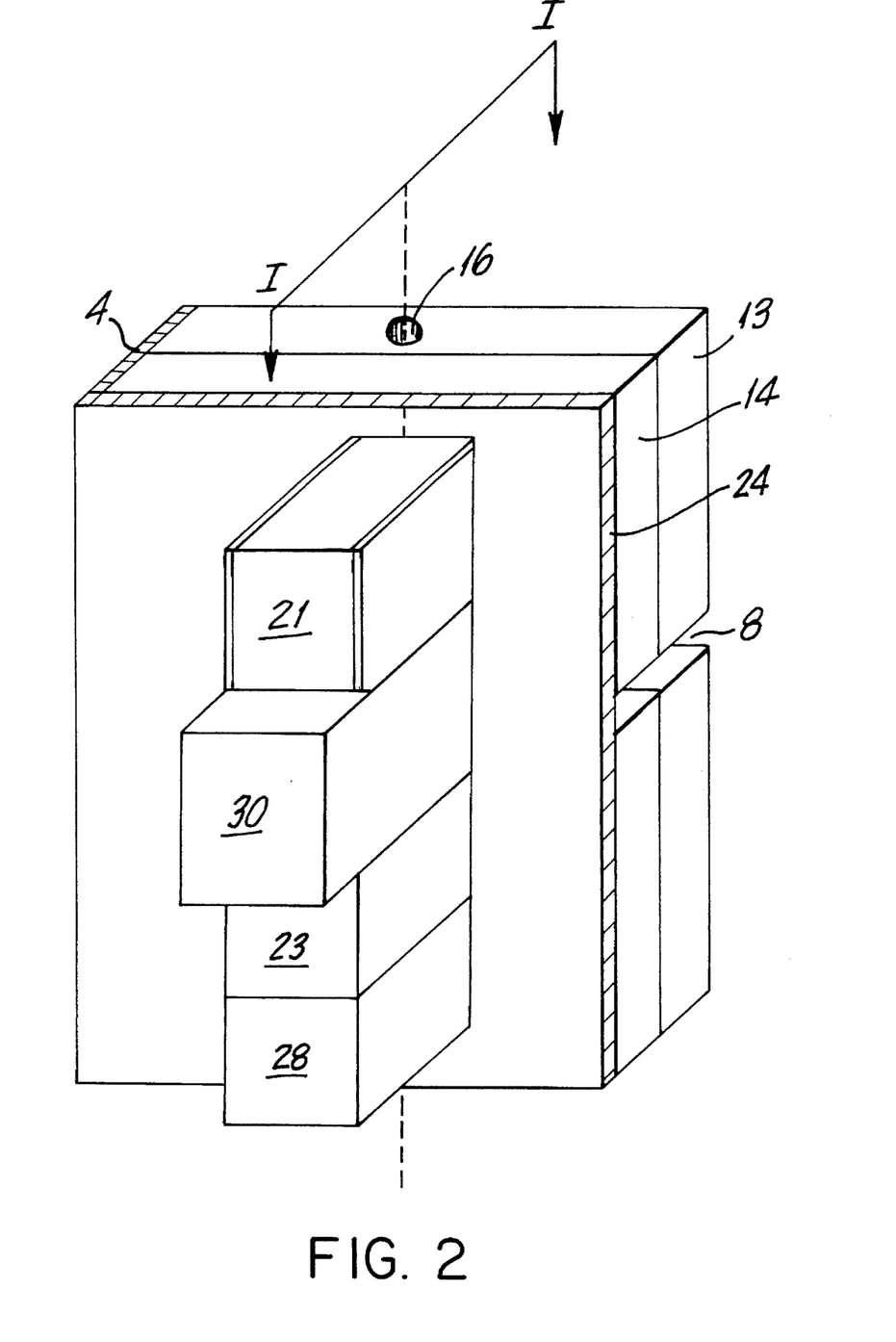
FIG. 2 shows the pump actuating device B1 of the cassette infusion system in accordance with FIG. 1 after mounting the infusion pump cassette A1 as seen in perspective from the front and below with the housing removed.

FIG. 2 shows the infusion pump actuating device B1 with the inserted infusion pump cassette A1 in perspective from the front and below after removal of the cover hood 1, on the plane of section I-I. After removal of the cover hood 1, a pneumatic inlet valve control cylinder 21, an outlet valve control cylinder 23 and furthermore a pump cylinder 30 together with an adjustable pressure sensor 28 will become apparent on the mounting plate 24. These cylinders are controlled via electropneumatic transducers 5 and (see FIG. 3).

Figure 3:
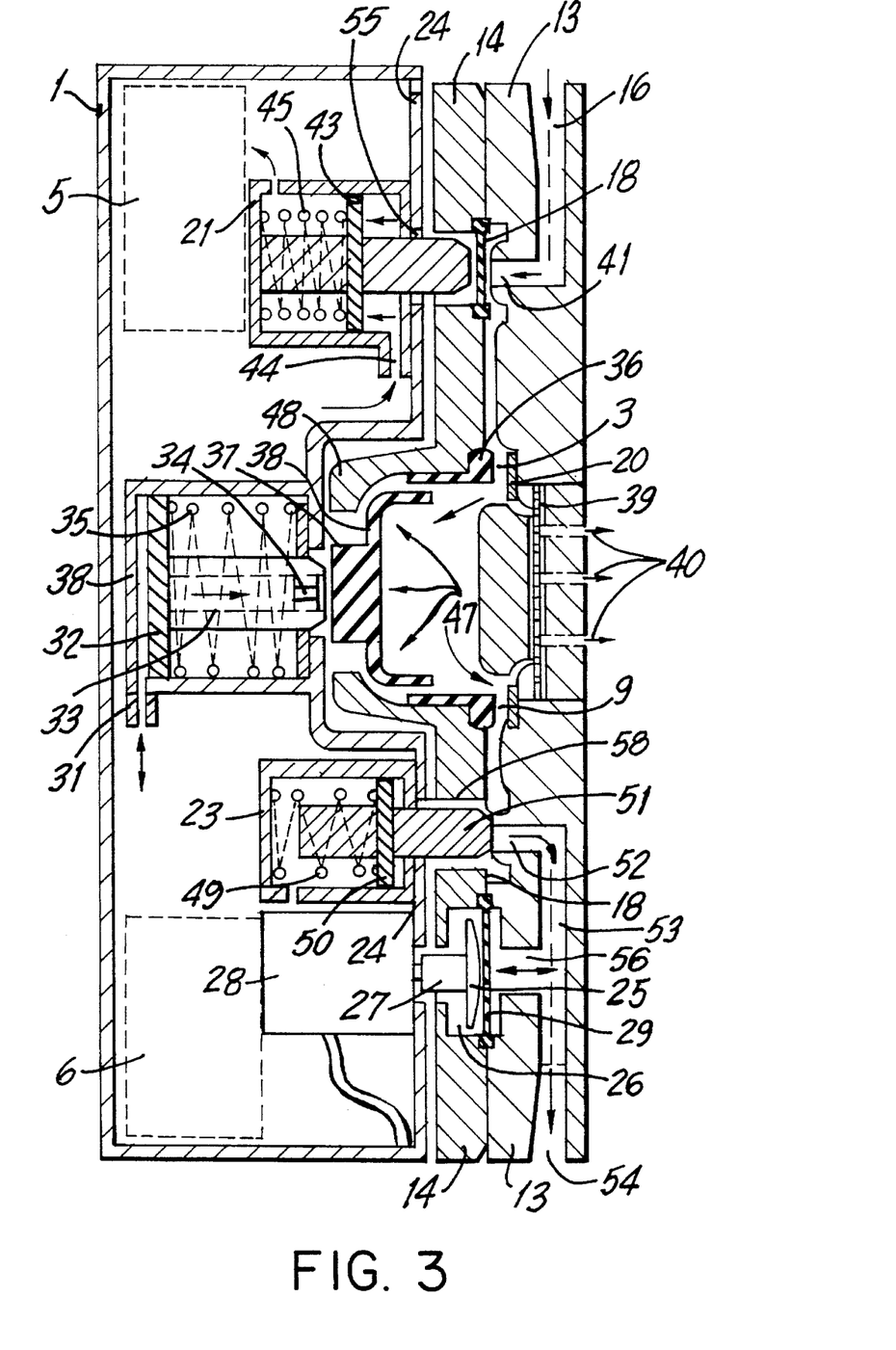
FIG. 3 shows a cross section taken through the pump actuating device in accordance. In the section line I-I in FIG. 2.

FIG. 3 shows the infusion actuating device B1 after insertion of the infusion pump cassette A1 in a section taken on the line I-I of FIG. 2. Looking from the left to the right, it is possible to see the cover hood 1 for the mounting plate, 24. On this plate the infusion pump cassette A1 is mounted together with its base plate 14 and cover plate 13. On looking at the figure from the top to the bottom, it will be that, as made clear by the arrows, there is a flow of the infusion solution (coming from an infusion container (not illustrated) with an infusion line and a Luer connection cone) via the conical inlet opening 16, as depicted, to the valve seat 41 molded in this plate. The elastic valve plate 18 marked in black and arranged in the space thereover, is compressed by the valve plunger 42 of the valve 21, since the piston 43 in the cylinder, as indicated by arrows, thrusts back the valve plunger 42 by way of the compressed air, entering via the port 44, against the force of a compression spring 45. By way of the valve, opened in this fashion, infusion liquid flows via an inlet tunnel 3 underneath a roll diaphragm sealing flange 36 into the pump chamber 47, which is constituted by the roll diaphragm 38 with its sealing flange 36 and the cover plate 13 as a cover. In this cover, fine holes 22 are arranged, which with a gap space having a hydrophobic diaphragm 39 (arranged over it) and furthermore venting openings 40 leading to the outside represent a venting filter for the pump chamber and the infusion liquid.

After the pump chamber has been completely filled, it is possible then, by entry of compressed air into a pump cylinder 30 through ports 31 and by pressure acting via a thrust plate 37 arranged on the floor of the roll diaphragm, for the pump chamber to be evacuated. The thrust plate 37 consists of ferromagnetic material. During evacuation of the pump chamber by means of the entering compressed air a piston 32, having a plunger tube 33 mounted thereon, is thrust against the force of a compression spring 35. At the tip of the plunger tube 33, an inductive distance sensor 34 is provided. During the evacuation of the pump chamber the outlet valve 23, which has been shut during the pump chamber filling phase, will be opened. FIG. 3 shows that in the shut state a compression spring 49 thrusts a piston 50 with a valve plunger 51 against the elastic valve plate 18 and that in this manner the valve seat 52 molded in the cover plate 13, of the valve 23 will be shut. Accordingly, no liquid is able to pass into the duct 56 for the pressure measuring chamber 26 with the pressure measuring plunger 27 and then via the infusion hose 19 inserted into the conical opening 54, to the patient connected with the system. If however the outlet valve is opened by inflow of compressed air, it is possible for the pump chamber 47 to be evacuated via the outlet tunnel 9 underneath the roll diaphragm sealing flange 36, the valve seat 52, the duct 53 and the infusion hose inserted into the opening 54.

In the following, the infusion pump cassette A1 will be described. It consists (see FIGS. 4 through 6) of two transparent synthetic resin, molded rectangular plates 13 and 14 held together under force, between which the two elastic valve plates 18 and, additionally in a cylindrical chamber 48, a pump roll diaphragm 38 with a thrust plate 37 and a further cylindrical chamber 26, and a pressure measuring diaphragm with a measuring plunger 27 are assembled.

Figure 4:
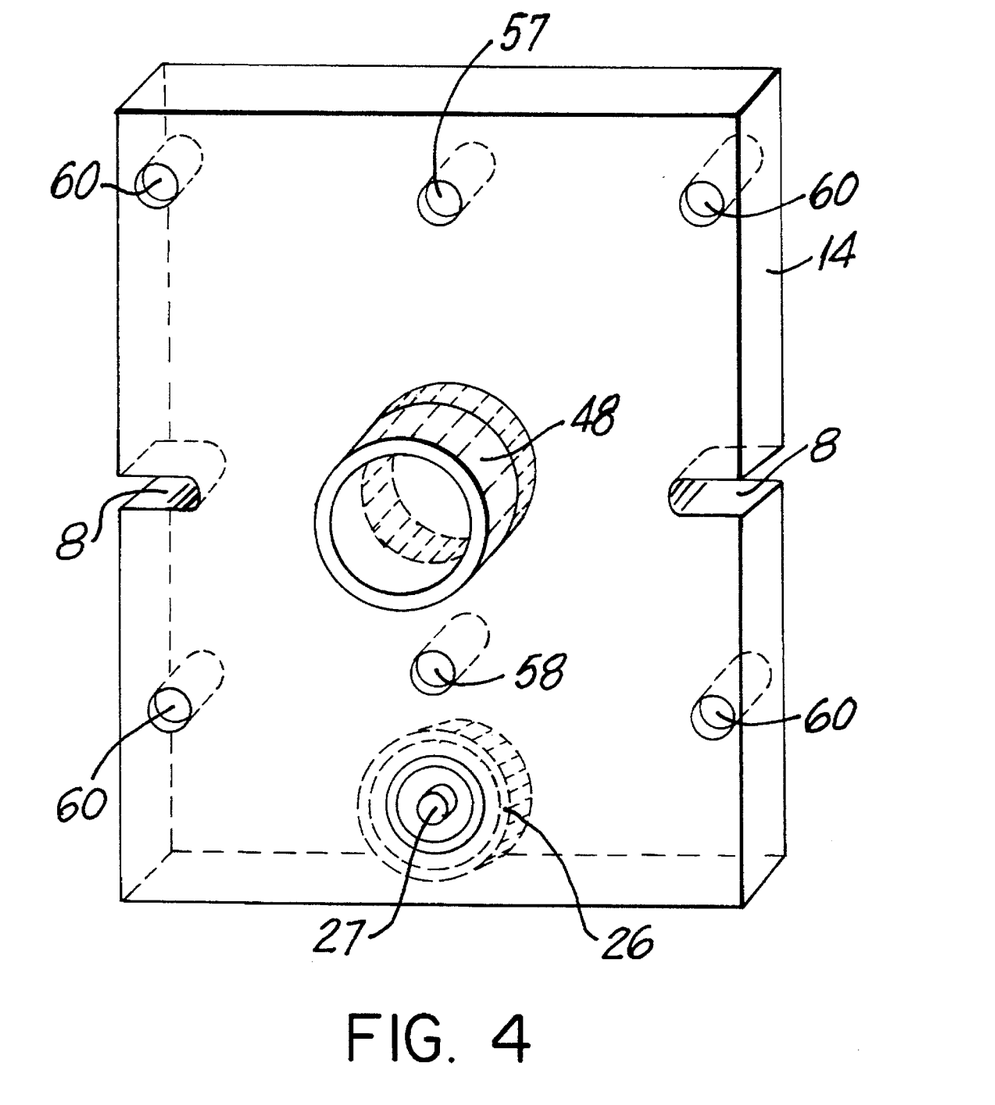
FIG. 4 shows a base plate of an infusion pump cassette as in FIG. 1 in perspective from below and with the pressure measuring plunger inserted.

FIG. 4 shows the base plate 14 in perspective from below. The plate 14 comprises, in addition the four openings 60 of the welded-on connecting bolts 12, openings for the inlet valve plunger 57, and the valve plunger opening 58 for the outlet valve 23. Adjacent to this over the plunger opening 58 there is a cylindrical opening in the plate 14, which is continued in a guide and protective cylinder 48 mounted thereon and connected firmly therewith, for the pump roll diaphragm 38. To the right and left thereof there are identical slots 8 for the attachment clips 10 and 11 (see FIG. 1). In the plate 14 underneath the opening 58, there is furthermore the cylindrical pressure measuring chamber 26 with the pressure measuring plunger 27 set therein.

Figure 5:
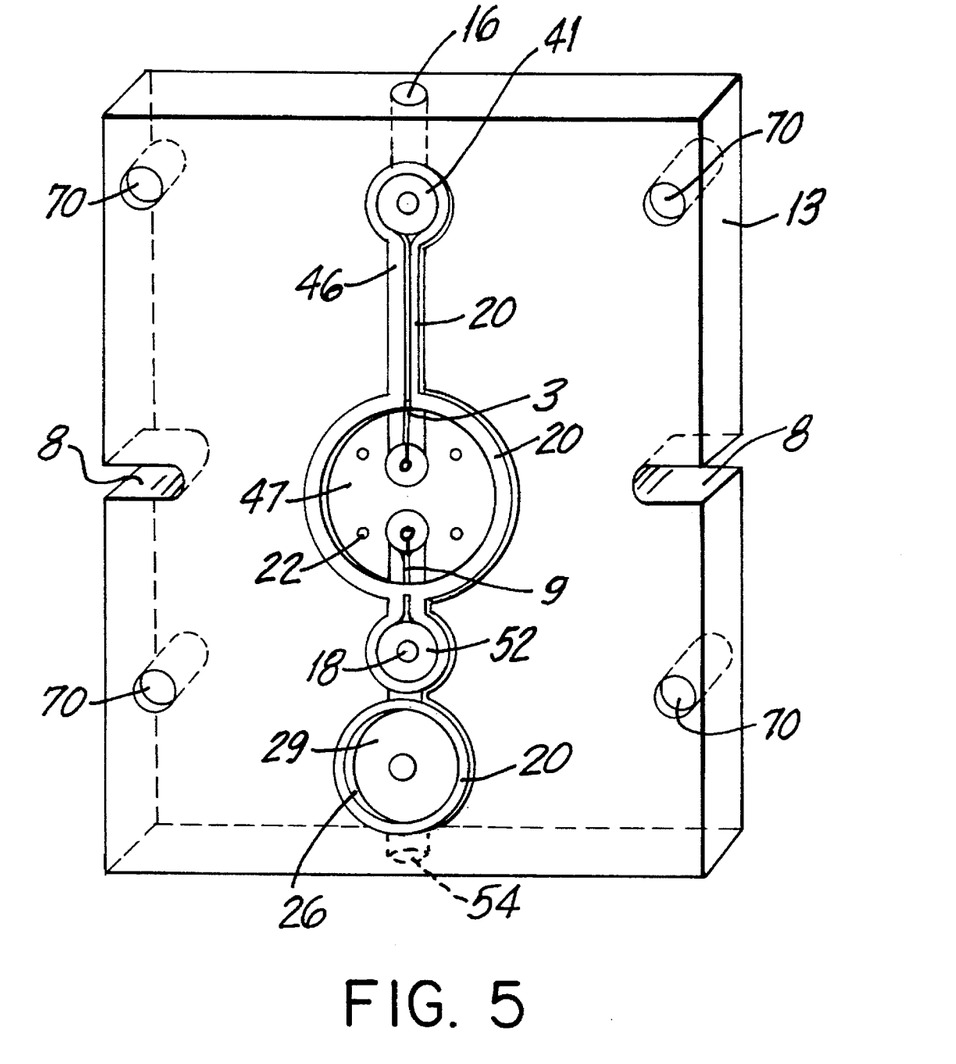
FIG. 5 shows a cover plate of the infusion pump cassette according to FIG. 1 in perspective from below, the elastic valve plate, which is shaded and shown as being transparent with a black edge, being inserted and a pressure measuring diaphragm being present.
Figure 6A:
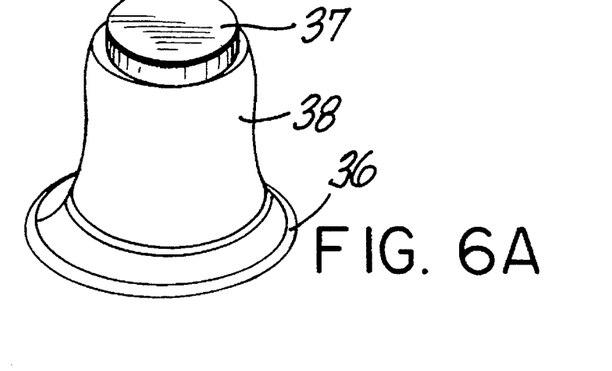
FIG. 6 shows separate parts of the pump chamber in accordance with the embodiment illustrated in FIG. 1 in an exploded view.
Figure 6B:
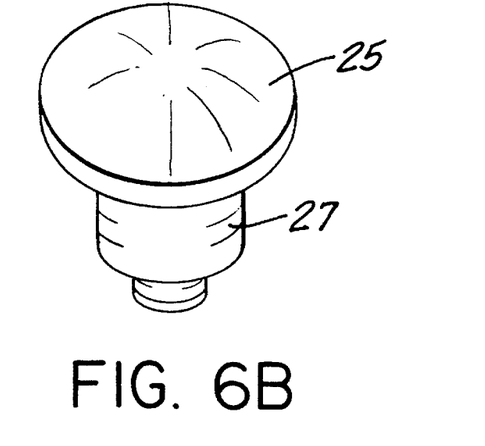
Figure 6C:
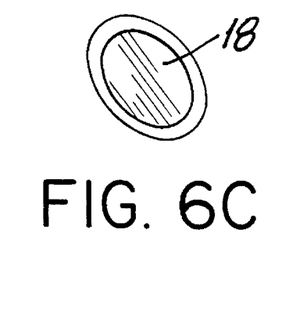
Figure 6D:
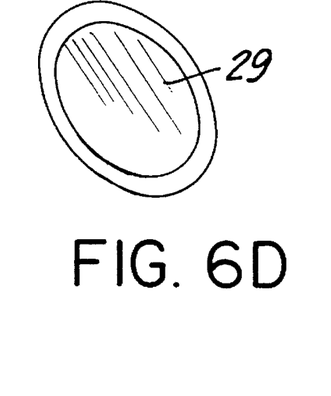

In FIG. 5 the cover plate 13 of the infusion pump cassette A1 is seen from below with the inserted elastic valve plates 18. The valve plates are transparent and shaded in the drawing and have edges shown in black. By way of the conical inlet opening 16 and the associated valve seat 41, liquid can be dispensed through the duct 46 covered by the sealing base plate welded in position and the supply duct tunnel 3 covered by the roll diaphragm flange 36, into the pump chamber 47. Here a plurality of connecting openings 22 is provided leading to the venting filter 39, which is arranged on the opposite side of the plate 13 (see FIG. 3). The evacuation of the pump chamber may take place via the outlet tunnel 9, which is also covered over by the sealing flange 36, via a connecting duct to the valve seat 52 and via the duct 53 (see FIG. 3) leading to the pressure measuring chamber and via the infusion line 19 inserted into the connection cone 54 leading to the patient.

The valve seats, the ducts, the pump chamber and the pressure measuring chamber are respectively surrounded by a raised edge. The same constitutes a sealing rail 20 to provide a sealed, welded connection between the base plate and the cover plate of the cassette. Four openings 70 serve for the additional introduction of the welded-on connecting, bolts 12.

In a perspective view, FIG. 6 shows the five additional parts inserted between the plates 13 and 14 of the infusion pump cassette A1, that is to say:

1 the pump roll diaphragm 38 with the sealing flange 36 and the thrust plate 37 permanently secured to the floor, of ferromagnetic material, 2 the pressure measuring plunger 27 with a vaulted upper surface 25, 3 and 4 two valve plates with a sealing edge 18 and 5, the pressure measuring diaphragm with a sealing edge 29.

Figure 7A:
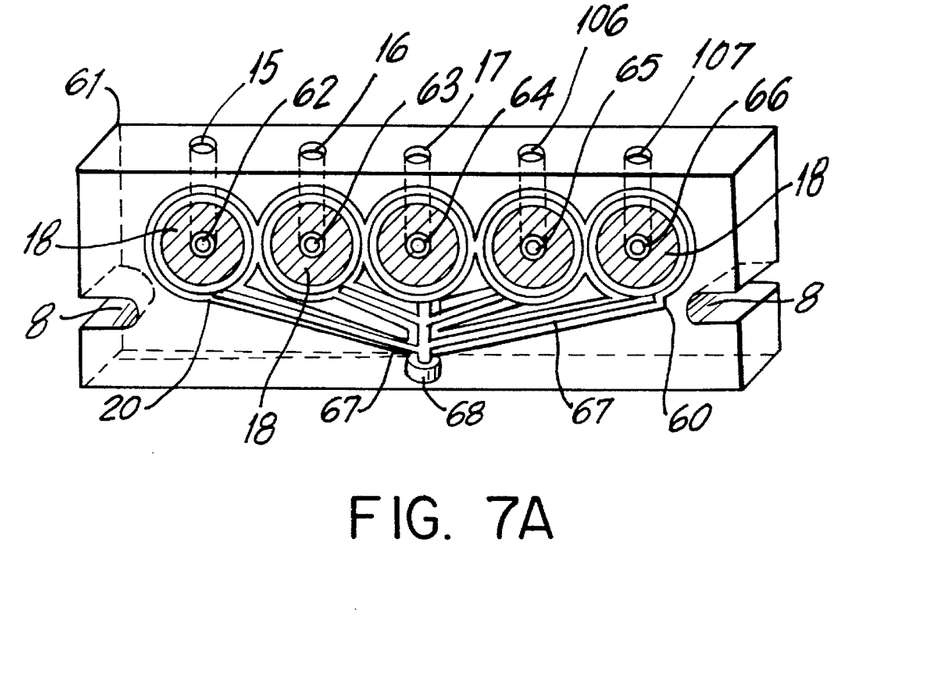
FIG. 7 shows the base the cover plates of an infusion distribution cassette with five inlets in accordance with the present invention as seen in plan view from the front and the top.
Figure 7B:
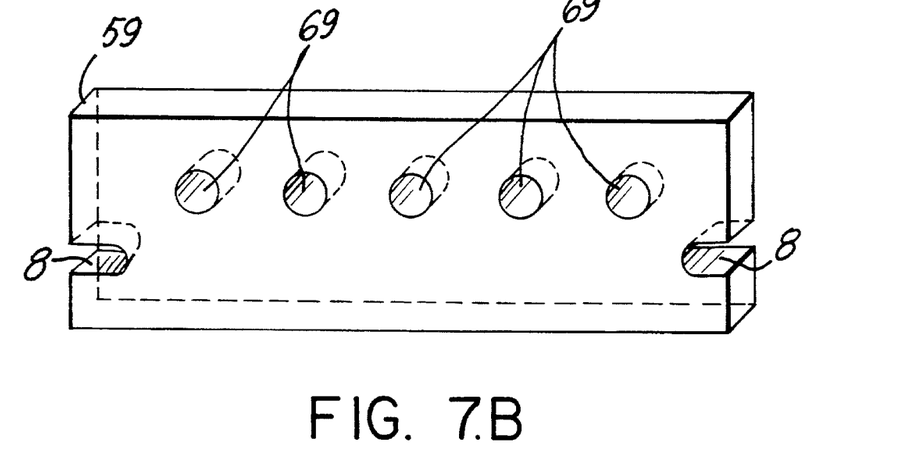

In the following an infusion distribution cassette will be described with reference to FIG. 7. It consists of two rectangular plates 59 and 61 molded using transparent synthetic resin, between which the five elastic valve plates 18 are inserted. FIG. 7 shows in perspective from below the base plate 59. In addition to the five inlet valve plunger openings 69 it possesses identical slots 8, on the right and left narrow sides, for attachment clips. The covering plate 61 possesses five inlet openings 15, 16, 17, 106 and 107, which are continued into the respective valve seats 62, 63, 64, 65 and 66, into which five elastic valve plates are inserted. As the reader will see, the valve seats are continued in discharge ducts 67, which then open into a common outlet opening 68. By way of the sealing rails 20 the covering plate 61 and the base plate 59 are welded or bonded under pressure to the inserted valve plates 18 so that the infusion distribution cassette is produced. The same is then attached with its slot-like recesses 8 on the narrow sides using clips on the valve pump syringe actuating device B 2 (see FIG. 8).

In the following, the course of an infusion operation will be described with reference to FIGS. 3, 7, 8 and 9. Together with their delivery hose (see FIG. 9) the five partly filled infusion containers 71, 72, 73, 74 and 75 are suspended using a conventional hanger 76 approximately 1 meter or even higher above the level of the heart of the patient. The ends, which are provided with standard Luer connected cones, of the delivery hoses are respectively inserted into the conical inlet openings 15, 16, 17, 106 and 107 of the infusion distribution cassette D. They are consequently connected via a respective inlet valve 83, 84, 85, 86, 87 and discharge ducts 67 with the outlet cone 68 (see FIG. 7) and via a connecting hose inserted therein with the infusion pump cassette A 2 and the inlet valve 7 thereof and furthermore with the associated pump chamber 47 thereof and the outlet valve 23. This outlet valve 23 is connected via a duct with the pressure measuring chamber and the pressure measuring sensor 28, the outlet valve 93, the pump chamber 89 and the outlet cone 119, over which the short infusion hose 19 having the hollow needle 81 for liquids is slipped. The pump chamber 89 is connected via its inlet valve 91 and a connecting hose 99, inserted at this position, with the outlet 109 of the medicament administration cassette E and therefore renders possible, in a manner independent from the infusion therapy taking place via the pump chamber 47, a simultaneous substantial continuously or furthermore intermittent supply of medicaments into the same vein of the patient.

Valves, ducts and chambers of the infusion distribution cassette and of the infusion pump cassette A 2 and of the connected and infusion hose are now filled with the infusion solution free of air bubbles prior to connection with the patient. Because of the manufacture of the infusion cassettes using transparent synthetic resin, this operation is substantially facilitated. Furthermore the automatic venting of the pump chamber is convenient in this respect. An automatic venting filter, familiar to the man in the art, may be integrated in addition between the outlet valve 23 and the outlet cone 54 in the infusion pump cassette, although it is not illustrated here.

After turning on the electronic, manually programmable microprocessor control device C 79, which may be arranged at some distance from the patient, the infusion program is commenced. It begins with the command to insert the infusion cassette. The cassettes A 2 and D may now be introduced into the valve and pump actuating device B 2. After proper insertion of the cassettes A 2 and D a test program is started with a completely automatic check on the infusion system as will be familiar to the man in the art. It is only after successful performance of such test that the infusion operation is enabled with the possibility of manual preprogramming of the desired infusion program (quantity, time, type of solution, mode of administration, order etc.) using the control device C 79.

After making the infusion connection with the patient (insertion of the vaned hollow needle 81 into a vein 82 in the patient's arm 80), the start button on the control device C 79 is depressed to begin the infusion operation. In accordance with the program, infusion solution, for instance, will flow from the container 74 (see FIG. 9 and FIG. 3) via the connection 16, the open valve seat 41 of the valve 21—the cylinder of the valve being under pressure—the tunnel 3 to the pump chamber 47, i.e. primarily to a gap space between the thrust plate 13 and the pump roll diaphragm 38. Under the hydrostatic pressure of the inflowing infusion solution this space steadily increases in size owing to downward thrusting of the roll diaphragm bottom with the thrust plate 37 toward the pump plunger tube 33, since the valve 23 at the outlet of the chamber 47 is shut. The valve plunger 51 is thrust by the compression spring 49 onto the valve plate 18 and the valve seat 52. When in approximately 2 to 3 seconds the pump chamber with its small volume is completely filled, the ferromagnetic thrust plate 37 on the floor of the roll diaphragm 38 activates the inductive distance sensor 34 in the pump plunger tube 33. Acting via the microprocessor control device C 79 and the electropneumatic transducers 5 and 6, the sensor causes the closing of the pneumatically operated valve 21. The valve cylinder is free of pressure and the plunger 42 is thrust by the compression spring 45 against the valve plate 18 and the valve seat 41.

The pump chamber 47, which is closed toward the inlet valve, is acted upon by the preprogrammed infusion pressure via the pump cylinder 30 activated by the electropneumatic transducers 5 and 6 by way of its plunger 33, the thrust plate 37 and the floor of the roll diaphragm 38. Because of the following opening of the outlet, infusion liquid is supplied quickly under pressure via the duct 53 from the connection duct 56 to the pressure measuring chamber 26, the connection 54, the infusion hose 19 and the vaned hollow needle 81 leading to the patient 82. The opening of the outlet valve 23 is performed by discharged of compressed gas from the electropneumatic transducer, the application of pressure on the piston 50, compression of the compression spring 49, drawing back of the valve plunger 51, relief of the valve plate 18 and opening of the valve seat 52. In order to render it possible for an evacuation of liquid also to take place in a protracted form into the vein as well precisely, the preselected microprocessor programs have available rapid or slow opening frequencies, long or short opening periods or variations in the opening and closing periods of the outlet valve 23 to vary the dosage rate.

In order to be able to define such minute individual dosages more exactly as a volume/time unit, the inductive distance sensor 34 is not only in a position to indicate the complete filling and evacuation of the pump chamber 47, but to perform the same in more than ten individual steps during evacuation of the same. By using a suitable algorithm, which links the stepwise pump evacuation with the opening time of the outlet valve, it is possible however, without any spurious effects due to the electropneumatic transducers 5 and 6, due to the pneumatic cylinder of the valve, or due to the adjustment of the valve plunger or the like, to ensure exact administration of fractions of the pump chamber volume with the aid of microprocessor control device C. If the pump chamber 47 is completely evacuated or empty, then this will be also recognized by the inductive distance sensor 34 using the thrust plate 37 of ferromagnetic material secured to the floor of the roll diaphragm 38, using the microprocessor control device C 79. There will then be a venting of the valve cylinder 23 and of the pump cylinder 30 via the electropneumatic transducers 5 and 6. The valve 23 will close, the compression spring 49 will, with the aid of the plunger 51 and the valve plate 18, shut off the valve seat 52 and the pump cylinder plunger tube 33 will be moved back by a compression spring 35 into the neutral position thereof. It is now possible for a renewed filling of the pump chamber 47, as described above, to be started. Dependent on the infusion program the filling is performed in alternating succession from the five infusion containers 71, 72, 73, 74 and 75.

If, for example, after a long period of infusion, some of the infusion containers have been emptied and, if, in accordance with the preselected program infusion liquid is still required from the same, it is not possible for the pump chamber 47 to be filled any more despite the inlet valve being open, as soon as the hydrostatic pressure in the infusion chamber with its outlet hose has gone below 100 cm water head. This necessary filling pressure is occasioned by the material of the roll diaphragm 38 or may be achieved in combination with a compression spring (not illustrated) acting on the bottom thereof with the thrust plate 37. Accordingly, the aspiration of air into the pump chamber 47, with possibly following infusion, is safely precluded. If however the pump chamber, for example, can no longer be completely filled with infusion liquid, there will be no signal from the distance sensor 34 in the time set by the microprocessor control device. This causes the production of an optical and acoustic alarm.

If, for example, the patient is suffering from serious disorders of the blood vessels with the danger of rapid thrombosis, it is then possible, for instance by the additional connection of an infusion container with flushing solution and by taking into account of such condition when preprogramming the infusion, for the microprocessor control device not only to raise an alarm when the infusion bottle is empty, but furthermore to cause a switching over to flushing solution and continuation of the infusion at a minimum rate. It is not only such trouble conditions during filling of the pump chamber, but also trouble conditions during emptying in a microprocessor-controlled time which is not adequate, which lead to the giving of an alarm signal. Such failures may for example be due to a complete breakdown of infusion—owing to a blocked, dislodged hollow needle 81 and a kinked infusion hose 19 can be indicated. However, they may merely indicate a partial dislodgement of the hollow needle with the accompanying increase in resistance to flow, something which might possibly be compensated for increasing the pump pressure. Furthermore, an excessively rapid evacuation as suddenly detected by the micro-processor control device may be responsible for an alarm. Any excessively rapid emptying may for instance be caused by detachment of the infusion hose, the infusion liquid the escaping into the surroundings unused.

Furthermore, using the monitoring, which is preselectable over a wide range using the adjustable pressure sensor 28, of the infusion pressure it is possible to obtain further safety functions for the patient. Thus, for instance, in the case of a preselected pressure values, it is possible to recognize not only a part of the above mentioned trouble conditions. Furthermore a dislodgement of the hollow needle or a perivenous infusion may be recognized. A possible high pump chamber pressure setting renders possible for instance however also the supply of sufficient infusion volumes.

In addition to such safety functions, numerous other safety measures for the apparatus are adopted. Thus failure of the electrical power supply will be responsible for an alarm and for the closure of all inlet valves 83 through 87 of the infusion distribution cassette D. In the case of the infusion pump cassette A 2 the inlet valves 7, 91, the outlet valves 23 and 93 will be closed and the pump chambers 47 and 89 will experience pressure relief owing to spring force and the venting of all actuating cylinders. A failure of the compressed gas supply will lead to an alarm being given, to closure of the inlet and outlet valves by spring force and to an easing off of the pressure in the pump chambers (pump cylinder in the neutral setting). Because of the pneumatic valve and pump actuation no electrically conducting connection is to be expected via the infusion solution to the patient.

Because of the use of sterile disposable infusion cassettes it is possible to do without sterile infusion hose, distributors, 3 way cocks, valves, pump hose, pump cylinders, syringes, venting filters and the like necessary with conventional equipment. Because of the additional dispensing with manual assembly and manual operation this leads to the following advantages:

1 less danger of bacterial contamination, 2 a substantial simplification of operation, 3 an enhanced freedom from errors in operation, 4 a substantial saving in labor and costs and 5 an optimum adaptation to the patient (owing to the modular design of the system).

This electropneumatic design described as an example supra may however be modified for purely electrical or hybrid electromechanical and pneumatic operation. In this respect for instance the electromagnets or pneumatic cylinders will act via plungers, the inlet and outlet valves and the pump chambers may be evacuated by an plunger advanced by an electric stepper motor in accordance with a program, for instance in a large number of small steps or in a few large ones in a pulsating manner with the outlet valve opened.

Figure 8:
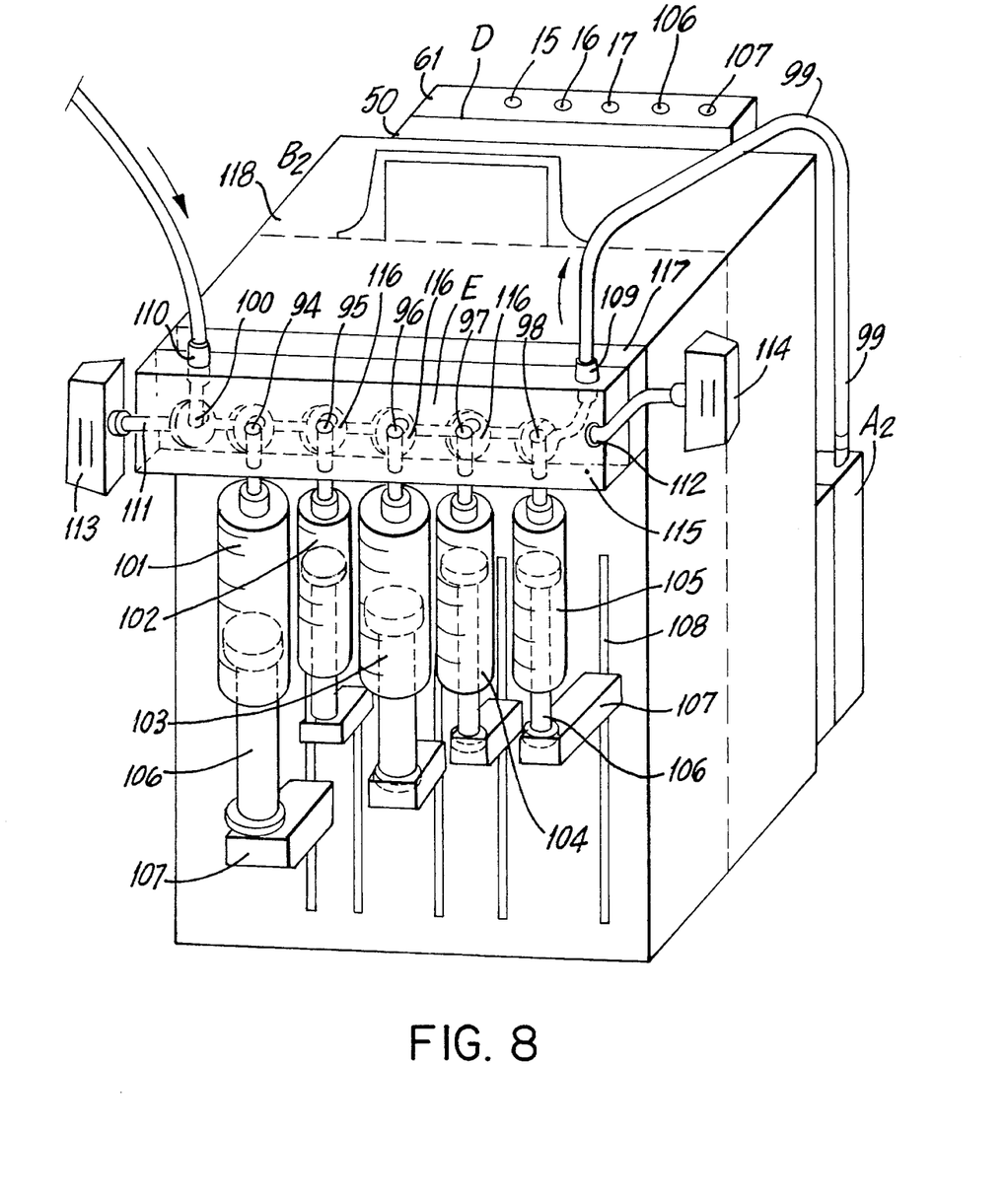
FIG. 8 shows a universal valve pump syringe actuating device with cassettes fitted on both sides in accordance with one embodiment of the invention.

With reference to FIGS. 8, and 9, a further simplification of infusion therapy with the cassette infusion system will be described for intensive care patients. In this case such programmed infusion therapy is combined with an automatic medicament administration.

In accordance with FIG. 8 the medicament administration apparatus is arranged on the valve pump syringe actuating device B 2 referenced 118. The device comprises the sterile medicament administration cassette E designed to be disposable, i.e. to be employed once only. It possesses a covering plate 115 with six valve seats 100, 94, 95, 97 and 98. The valve seats are, in design, equivalent to the ones described supra. They are connected both with the inlet connector 110 and the outlet connector 109 and furthermore with each other with the aid of ducts. The valve seats 94, 95, 96, 97 and 98 are provided respectively with a standard Luer connection port for locking with the marked sterile disposable plastic syringes 101 through 105 serving as medicament containers. Underneath the covering plate 115 there follow the six elastic valve plates 116, mounted in the valve seats, and underneath the same there is finally the floor plate 117 provided with plunger openings. The design is generally similar to that of FIG. 7. The two plates are connected together under pressure in a sealing manner at their sealing rails or strips using welded-on bolts (not illustrated as such). By means of the spring-loaded clip closures 113 and 114, which in the present case are depicted in the released state, the medicament cassette E is firmly secured on the valve pump syringe actuating device B 2 referenced 118 with its valve plungers for the valves 100, 94, 95, 96, 97 and 98. The piston rods and pistons of the disposable syringes 101 through 105 are drawn upward with the aid of strong tension springs, arranged in the valve pump syringe actuating device B 2, acting through slides running in slots 108 so that the contents of the syringe are put under pressure.

In what follows, the function of the medicament administration device of the cassette infusion system will be described with reference to figures 8 and 9. In FIG. 9, the individual functional elements are illustrated diagrammatically. Encircling lines serve to indicate their association with the module of the cassette infusion system, i.e. with the modules A, B, C, D and E. A 2, B 2 and D correspond to the double infusion pump cassette in combination with the valve pump and syringe actuating device and the infusion distributing cassette D. C corresponds to the microprocessor control device with pneumatic means and E and B 2 correspond to the medicament administration device in combination with the valve publication actuating device. Additionally, the reader will see the six connected infusion containers 71, 72, 73, 74, 75 and 88, the site of infusion, the arm 80 in the vein 82 of the patient. The six infusion contents are carried on a conventional hanger stand 76 approximately 1 meter or more above the level of the patient's heart. The discharge hoses connected by standard connectors are respectively connected with the inlet connectors of the cassettes 110, 107, 106, 12, 16 and 15 so that they are accordingly connected with a respective inlet valve 100, 83, 84, 85, 86 and 87. The inlet valves 83 through 87 of the infusion distributing cassette D are for their part connected via ducts with the outlet 68 thereof and connected by means of the connecting hose inserted here, with the double infusion pump cassette A 2 and the inlet valve 7 thereof, the pump chamber 47 and the outlet valve 23 thereof.

The medicament administration cassette E is connected via its connection hose 99 with the inlet valve 91 of the pump chamber 89 and the outlet valve 93 thereof. The two outlet ducts of the outlet valves are combined as a common duct, which with a shunting function connects the pressure measuring chamber 26 with the infusion pressure sensor 28 and at its end bears a standard connector 119 for connection with the infusion hose 19 and the vaned hollow needle 81.

The valves, the ducts and the pump chamber etc. of the three cassettes, that is to say of the double infusion pump cassette A 2, of the infusion distributor cassette D and the medicament administration cassette E are charged with infusion solution in a fashion free of bubbles. The disposable syringes 101 through 105 filled with the desired pharmacological preparations free of bubbles are now locked with the cassette E adjacent to five standard Luer connections as illustrated. The prepared cassettes are placed in holding means of the valve, pump, syringe actuating devices B 2 with the modules 118 (FIG. 8) to the left and the right and secured in position by means of clips 113 and 114 (shown in the released condition). Using the five spring-loaded slides 107 by means of the piston rods and pistons of the disposable syringes the content thereof is put under gage pressure for the systematic discharge thereof into the cassette A 2.

For the transfer of the medicaments into the double infusion cassette A 2 a narrow bore hose 99 is employed which is attached to the outlet 109 of the medicament administration cassette E and which has its connector locked with the inlet port of the inlet valve 91 of the cassette A 2. The infusion operation using the cassette A 2 has already been described at length. Here only a few particular details will be described in connection with the employment of the medicament administration device and the cassette A 2 (see FIG. 9) provided with two pump chambers.

If in accordance with the program set at a particular time the administration of the medicament is desired, for instance through the syringe 101, the microprocessor control device C referenced 79 will activate the valve, pump, and syringe actuating device B 2. By means of plungers, the valves 94 and 91 are opened. Accordingly the medicament solution under gage pressure is able to flow through the transfer hose 99 and the valve 91 into the pump chamber 89. When filling is completed the valves 91 and 94 are shut. The program control now causes the pump chamber 89 to be put under pressure slowly, rapidly or in steps with the outlet valve 93 open. Accordingly the medicaments are transferred through the hollow needle 81 into the arm vein 82 of the patient.

Independently of such medicament administration simultaneously, it is possible for infusion solution to be supplied from the containers 71, 72, 73, 74 and 75 via the associated inlet valve 7 and the pump chamber 47 and the outlet valve 23 to the patient. In order to avoid mixing medicaments which are incompatible, and, furthermore, inaccurate dosage with medicaments because of residues of medicaments in the valve seats and ducts in the cassette E, as well the transfer hose 99, the inlet valve 91 of the pump chamber 89, with the associated pump cylinder 90, the level sensor elements 92 and the outlet valve 93, it is possible, after each administration of medicaments to employ the infusion solution 88, for instance an indifferent physiological saline solution to flush the above mentioned hose, valves, ducts and chambers, by opening the valve 100, so that such solution laden with medicament residues is supplied to the patient.

The level sensor elements for the pump chamber 89 render possible a dosage not only in full chamber volumes but furthermore in fractions thereof.

Using the above system it is possible to supply different medicament and infusion solution continuously in sequence and at different times to the patient. The supply may be furthermore exactly checked by the electrical microprocessor control device and a record kept of the operations using a printer connected with the equipment.

I claim:

1. A modular cassette infusion system for multiple infusions with a special suitability for intensive care comprising at least the following modules:
   a) an infusion pump cassette comprising at least one pump chamber with an inlet duct, an inlet valve, an outlet duct and an outlet valve,
   b) an infusion distributor cassette, which has two or more connections for infusion lines with associated inlet valves and following liquid distribution ducts, which open into one or more outlet connections,
   c) a disposable medicament administration cassette comprising a plurality of medicament containers respectively connectable to one another and to an outlet connection of the medicament administration cassette,
   wherein the outlet connections of the infusion distributor cassetter are connected to the inlet valve of the at least one infusion pump cassette via a connection hose,
   the outlet connection of the medicament administration cassette is connected to an inlet valve of a further pump chamber via a further connection hose, the further pump chamber further comprising an outlet valve, an inlet duct and an outlet duct,
   and the outlet ducts of the respective pump chambers are connectable to one another via their respective outlet valves.

2. The cassette infusion system as claimed in claim 1, characterized in that the infusion pump cassette additionally possesses a pressure measuring chamber and at least one venting filter.

3. The cassette infusion system as claimed in claim 1, characterized in that as an additional module the system comprises a valve, pump and syringe actuating device, which by means of plungers controls the valves arranged in the cassettes and the pump chambers and via metering plungers determines the infusion pressure.

4. The cassette infusion system as claimed in claim 1, characterized in that as an additional module the system comprises a microprocessor control device.

5. The cassette infusion system as claimed in claim 1, characterized in that the individual cassettes respectively possess bottom and covering plates of transparent molded plastic, which are fitted together in a sealing fashion by means of raised sealing rails on the covering plates and, respectively, the bottom plates, which surround all valve systems, open ducts, pump chambers and measuring chambers, and correspondingly shaped parts on the bottom and covering plates, and elastic valve plates, pump diaphragm and measuring diaphragm arranged between the bottom plate and, respectively, the covering plate are thrust together.

6. The cassette infusion system as claimed in claim 1, characterized in that the individual cassettes respectively possess bottom and covering plates of selectively transparent molded plastic, between which an elastic sealing plate is pressed.

7. The cassette infusion system as claimed in claim 1, characterized in that the infusion pump cassette additionally possesses a plurality of preferably cylindrically shaped cavities in its bottom plate and in its covering plate, into which cavities pump diaphragms provided with thrust plates, and pressure measuring plungers and, respectively, a pressure measuring diaphragm may be laid and into which a hydrophobic, air-permeable filter diaphragm is able to be pressed in a gas-tight manner.

8. The cassette infusion system as claimed in claim 1, characterized in that the valves are formed by the respective cassette covering plate with its integrally molded valve seats and inserted valve plates with a sealing edge and its associated supply and discharge ducts and the corresponding bottom plate with its valve plunger openings by welding or bonding of the valve seats and raised sealing surrounding the supply and discharge ducts.

9. The cassette infusion system as claimed in claim 1, characterized in that the pump chamber is passively filled by gravity infusion from one or more containers and in that the emptying thereof takes place actively by the displacement of a plunger.

10. The cassette infusion system as claimed in claim 1, characterized in that the pump chamber has a volume of 0.5 to 20 ml.

11. The cassette infusion system as claimed in claim 1, characterized in that the pump chamber comprises a non-extensible roll diaphragm and a thrust plate attached to the bottom thereof.

12. The cassette infusion system as claimed in claim 1, characterized in that a soft compression spring acts on the lower side of the roll diaphragm thrust plate and has an effect on the hydrostatic pressure necessary in the chamber filling phase.

13. The cassette infusion system as claimed in claim 1, characterized in that the pump chamber possesses a highly elastic planar diaphragm, a diaphragm with concertina folding or an elastic roll diaphragm with a thrust plate attached respectively to its lower side.

14. The cassetter infusion system as claimed in claim 1, comprising inductive or capacitive distance sensors for exactly measuring the level of filling of the pump chamber, which cooperate with the thrust plate of the pump diaphragm comprising ferromagnetic material.

15. The cassette infusion system as claimed in claim 1, characterized in that the chamber pressure of the pump chamber, which substantially is equal to the infusion pressure, is varied over a large range by changing the working pressure of a pump plunger medicament actuating cylinder.

16. The cassette infusion system as claimed in claim 1, characterized in that an inductive or capacitive distance sensor is provided in the valve plunger of the outlet valve, said sensor exactly indicating the opening and closing of the valve.

17. The cassette infusion system as claimed in claim 1, characterized in that hydrophobic venting filters, which are impermeable for liquids are provided in the infusion distributing cassette in the pump chamber cover and/or between the outlet valve of the pump chamber and the connection for the infusion hose leading to the patient.

18. The cassette infusion system as claimed in claim 1, characterized in that in the infusion pump cassette between the outlet valve from the pump chamber and the connection means for the infusion hose leading to the patient a cylindrical chamber is formed is covered over by an elastic sealing diaphragm on which a pressure sensor is engaged for the measurement of the infusion pressure.

19. The cassette infusion system as claimed in claim 1, characterized in that in the infusion distributing cassettes the valve seats, the liquid distributing ducts, the pump chambers, the pressure measuring diaphragm and the chambers with an air buffer function are provided respectively with surrounding sealing rails.

20. The cassette infusion system as claimed in claim 1, characterized in that the microprocessor control device causes the infusion liquid flow to the patient to be intermittent and with a distinct pulsating effect, the pump chamber being able to be completely emptied in one step with the respective outlet valve opened.

21. The cassette infusion system as claimed in claim 1, characterized in that the microprocessor control device ensures a fine control of the infusion liquid rate to the patient and in a substantially continuous manner by to stepped emptying of the pump chamber in substantially equal steps.

22. The cassette infusion system as claimed in claim 1, characterized in that the microprocessor control device causes a stepped evacuation of the pump chamber linked with an opening time of the outlet valve and consequently renders possible an exact discharge of part of a volume of the pump chamber.

23. The cassette infusion system as claimed in claim 4, characterized in that the microprocessor control device gives an alarm signal as a consequence of a disconnection of the hose.

24. The cassette infusion system as claimed in claim 1, characterized in that the microprocessor control device recognizes excessively long evacuation times for the infusion cassette pump, and in that accordingly an alarm is produced with an indication of an "obstruction".

25. The cassette infusion system as claimed in claim 1, characterized in that in the case of an excessively long filling time for the infusion cassette pump chamber the microprocessor control device causes an alarm with an indication that the infusion container is empty.

26. The cassette infusion system as claimed in claim 25, characterized in that the after the detection that an infusion container is emptied the microprocessor control device causes a switching over to an infusion container flushing solution and with a simultaneous reduction of the infusion rate to a minimum to keep open the vascular access.

27. The cassette infusion system as claimed in claim 1, characterized in that in the case of incompatibility of the infusion solutions the microprocessor control device ensures that such solutions are infused through one vascular access point, and an indifferent flushing solution is intermittently administered.

28. The cassette infusion system as claimed in claim 4, characterized in that the pump chamber evacuation rate is varied by the microprocessor control device in order to set the rate of infusion.

29. The cassette infusion system as claimed in claim 1, the medicament administration cassette accepts pressurized medicament containing disposable syringes, said syringes can be emptied by means of a special purpose valve and pump actuating device, which also cooperates with the infusion cassettes.

30. The cassette infusion system as claimed in claim 1, characterized in that a container filled with physiological sterile flushing liquid is connected with an inlet port of the medicament administration cassette, from which flushing liquid may emerge after each administration of a medicament in order to swill medicament residues from the medicament administration cassette, the connection hose and the infusion cassette into the vascular system of the patient.

31. The casseter infusion system as claimed in claim 1, characterized in that the medicament administration cassette comprises a covering plate with molded on valve seats and sealing rails and a bottom plate with associated valve plunger openings and intermediately arranged, pressed in elastic valve plates.

32. The cassette infusion system as claimed in claim 1, characterized in that within the medicament administration cassette the openings provide in the center of the valve seats, apart from the opening in the inlet valve, respectively communicate with Luer standard connection ports, the respective Luer and standard connection ports representing the connection element for the different disposable syringes.

33. The cassette infusion system as claimed in claim 1, characterized in that within the medicament administration cassette the gage pressure in the medicament filled disposable syringes is produced by means of cocked springs and thrust slides thereof and by plunger and pistons of the disposable syringes.

34. The cassette infusion system as claimed in claim 1, characterized in that the universal valve, pump and syringe actuating device comprises two half shells, into which the valve and pump cylinders are directly mounted and simultaneously serve as a housing for the device.

* * * * *

UNITED STATES PATENT AND TRADEMARK OFFICE
CERTIFICATE OF CORRECTION

PATENT NO. : 5,609,572
DATED : March 11, 1997
INVENTOR(S) : Volker Lang

It is certified that error appears in the above-indentified patent and that said Letters Patent is hereby corrected as shown below:

Claim 7, line 10, delete "may be" and insert -- are --; line 11, delete "able to be".

Claims 14 and 31, line 1, delete "cassetter" and insert -- cassette --.

Claim 21, line 19, delete "to".

Claim 26, line 44, after "container", insert -- with --; line 45, delete "with".

Signed and Sealed this

Twenty-fourth Day of June, 1997

Attest:

BRUCE LEHMAN

Attesting Officer

Commissioner of Patents and Trademarks